US011553943B2

(12) United States Patent
Chida

(10) Patent No.: US 11,553,943 B2
(45) Date of Patent: Jan. 17, 2023

(54) CATHETER SYSTEM AND TREATMENT METHOD

(71) Applicant: TERUMO KABUSHIKI KAISHA, Tokyo (JP)

(72) Inventor: Takahiro Chida, Kawasaki (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 934 days.

(21) Appl. No.: 15/073,118

(22) Filed: Mar. 17, 2016

(65) Prior Publication Data

US 2016/0270813 A1 Sep. 22, 2016

(30) Foreign Application Priority Data

Mar. 20, 2015 (JP) .............................. JP2015-058310

(51) Int. Cl.
*A61B 17/22* (2006.01)
*A61B 17/3207* (2006.01)
*A61B 17/221* (2006.01)

(52) U.S. Cl.
CPC ...... *A61B 17/320758* (2013.01); *A61B 17/22* (2013.01); *A61B 17/320725* (2013.01);
(Continued)

(58) Field of Classification Search
CPC ...... A61B 17/32002; A61B 17/320758; A61B 17/320725; A61B 17/320783;
(Continued)

(56) References Cited

U.S. PATENT DOCUMENTS 4,649,919 A * 3/1987 Thimsen .......... A61B 17/32002
30/133
4,669,469 A 6/1987 Gifford, III et al.
(Continued)

FOREIGN PATENT DOCUMENTS

JP S62-266046 A 11/1987
JP H02-011166 A 1/1990
(Continued)

OTHER PUBLICATIONS

Office Action (Notice of Reasons for Refusal) dated Nov. 25, 2019, by the Japanese Patent Office in corresponding Japanese Patent Application No. 2017-508206 and an English Translation of the Office Action. (10 pages).

(Continued)

*Primary Examiner* — Darwin P Erezo
*Assistant Examiner* — Erin L Colello
(74) *Attorney, Agent, or Firm* — Buchanan Ingersoll & Rooney PC

(57) ABSTRACT

A catheter system includes a shaft main body including an elongated hollow outer tube and an inner tube accommodated in the inside of the elongated hollow outer tube. The hollow inside of the inner tube is suctioned from the proximal end side thereof. The outer tube has an opening formed in a circumferential surface thereof and an attaching portion provided therein on the distal end side with respect to the opening. The inner tube can move in an axial direction with respect to the outer tube, and at least a distal end side end portion thereof can move back and forth between a proximal end side position with respect to the opening and the attaching portion. The inner tube has a cutting unit provided in the hollow inside of the distal end side end portion thereof and is capable of attaching to the attaching portion

19 Claims, 8 Drawing Sheets

(52) U.S. Cl.
CPC .... *A61B 17/320783* (2013.01); *A61B 17/221* (2013.01); *A61B 2017/22079* (2013.01); *A61B 2017/22094* (2013.01); *A61B 2017/320766* (2013.01); *A61B 2017/320775* (2013.01)

(58) Field of Classification Search
CPC ....... A61B 2017/320791; A61B 2017/320024; A61B 2017/320028; A61B 17/3207; A61B 2017/32004; A61B 17/22; A61B 17/221; A61B 2017/22079; A61B 2017/320775; A61B 2217/005; A61B 2018/00267; A61B 2017/320766; A61B 2017/320064; A61B 10/0283; A61B 10/0275; A61B 10/0266; A61B 10/02; A61B 5/150251; A61F 9/00763
See application file for complete search history.

(56) References Cited

U.S. PATENT DOCUMENTS

| | | | |
|---|---|---|---|
| 4,890,611 A | | 1/1990 | Monfort et al. |
| 4,994,067 A | | 2/1991 | Summers |
| 5,087,265 A | * | 2/1992 | Summers ....... A61B 17/320758 604/22 |
| 5,106,364 A | * | 4/1992 | Hayafuji .......... A61B 17/32002 30/208 |
| 5,368,603 A | * | 11/1994 | Halliburton .... A61B 17/320783 604/22 |
| 5,370,651 A | * | 12/1994 | Summers ....... A61B 17/320758 606/159 |
| 5,417,703 A | * | 5/1995 | Brown ................ A61B 17/22 606/159 |
| 5,431,673 A | * | 7/1995 | Summers ....... A61B 17/320758 606/167 |
| 5,490,859 A | | 2/1996 | Mische et al. |
| 5,526,822 A | * | 6/1996 | Burbank ............ A61B 10/0266 600/567 |
| 5,527,332 A | * | 6/1996 | Clement ........ A61B 17/320016 604/35 |
| 5,571,130 A | * | 11/1996 | Simpson ........ A61B 17/320783 606/159 |
| 5,649,547 A | * | 7/1997 | Ritchart ............ A61B 10/0266 600/566 |
| 5,733,297 A | * | 3/1998 | Wang .................. A61F 9/00763 606/167 |
| 6,024,751 A | * | 2/2000 | Lovato ................... A61B 1/015 604/22 |
| 6,156,049 A | * | 12/2000 | Lovato ................... A61B 1/015 604/22 |
| 6,443,959 B1 | * | 9/2002 | Beland ................ A61B 17/221 606/127 |
| 6,478,805 B1 | * | 11/2002 | Marino ................ A61F 2/4455 606/170 |
| 6,629,986 B1 | * | 10/2003 | Ross ................ A61B 17/32002 604/22 |
| 6,645,217 B1 | * | 11/2003 | MacKinnon ... A61B 17/320758 606/159 |
| 6,773,443 B2 | * | 8/2004 | Truwit ................... A61B 10/04 600/567 |
| 6,818,001 B2 | * | 11/2004 | Wulfman ....... A61B 17/320725 606/171 |
| 6,979,332 B2 | * | 12/2005 | Adams ............ A61B 17/32002 606/170 |
| 8,574,253 B2 | * | 11/2013 | Gruber ................ A61M 1/0082 606/171 |
| 8,641,640 B2 | * | 2/2014 | Lubock .............. A61B 10/0275 600/564 |
| 9,254,142 B2 | * | 2/2016 | Germain ........ A61B 17/320016 |
| 9,439,677 B2 | * | 9/2016 | Germain ................ A61B 1/015 |
| 9,439,720 B2 | * | 9/2016 | Germain ................ A61B 18/18 |
| 9,615,969 B2 | * | 4/2017 | Nissan ................ A61F 9/00763 |
| 9,655,639 B2 | * | 5/2017 | Mark ..................... A61B 1/018 |
| 9,743,979 B2 | * | 8/2017 | Germain ................ A61B 18/18 |
| 9,931,105 B2 | * | 4/2018 | Mark .................. A61B 10/0275 |
| 2001/0031981 A1 | * | 10/2001 | Evans ................... A61B 17/221 606/200 |
| 2005/0027210 A1 | * | 2/2005 | Miller ................ A61B 10/0096 600/567 |
| 2008/0249553 A1 | * | 10/2008 | Gruber ............ A61B 17/32053 606/171 |
| 2010/0036312 A1 | | 2/2010 | Krolik et al. |
| 2014/0171997 A1 | * | 6/2014 | Nissan ................ A61F 9/00763 606/171 |

FOREIGN PATENT DOCUMENTS

| | | |
|---|---|---|
| JP | H08-509639 A | 10/1996 |
| JP | 2011-522635 A | 8/2011 |

OTHER PUBLICATIONS

Office Action (Notice of Reasons for Refusal) dated Feb. 10, 2020, by the Japanese Patent Office in corresponding Japanese Patent Application No. 2017-508206 and an English Translation of the Office Action. (10 pages).

* cited by examiner

CATHETER SYSTEM AND TREATMENT METHOD

CROSS-REFERENCE TO RELATED APPLICATION

This application claims priority to Japanese Application No. 2015-058310 filed on Mar. 20, 2015, the entire content of which is incorporated herein by reference.

TECHNICAL FIELD

The present disclosure relates to a catheter system which suctions and removes a thrombus generated in a body lumen and a treatment method in which the catheter system is used.

BACKGROUND DISCUSSION

If a thrombus is generated in a body lumen, then it is necessary to quickly remove the thrombus. Deep venous thrombosis, in which a thrombus is generated in a vein existing in a deep part of the body such as, for example, a femoral vein or a popliteal vein, is conceivably a symptom of a thrombus having been generated in a body lumen. As a treatment method for deep venous thrombosis, a method is known in which a shaft main body of a catheter system is inserted into a blood vessel and then an agent such as a thrombolytic agent is injected into an embolus portion to thereby dissolve and remove the thrombus.

Since a side effect such as bleeding is involved in a known method in which an agent is injected in order to remove a thrombus, a treatment has been proposed in which a thrombus is mechanically broken and is suctioned out and removed by a shaft main body inserted in a blood vessel. By this treatment, it is possible to eliminate the use of the agent or reduce the amount of the agent to be used. As a catheter system for use for such a treatment as just described, for example, such a system is disclosed in U.S. Pat. No. 6,024,751.

When a thrombus is mechanically broken and suctioned out through a shaft main body, since the shaft main body has a tube body of a small diameter, there is the possibility that an intermediate location of the shaft main body may be clogged by the thrombus. If an intermediate location of the shaft main body is clogged by the thrombus, then it becomes difficult to suction out the thrombus. Therefore, it is necessary to suppress clogging of the shaft main body by the thrombus.

SUMMARY

The disclosure herein provides a catheter system in which a thrombus to be suctioned out is crushed so as to be smaller than an inner diameter of the shaft main body with certainty so that the thrombus can be suppressed from clogging the shaft main body and a treatment method in which the catheter system is used.

According to the disclosure, a catheter system is provided including a shaft main body having an elongated hollow outer tube and an inner tube accommodated in the inside of the elongated hollow outer tube, the hollow inside of the inner tube being suctioned from the proximal end side thereof, the outer tube having an opening formed in a circumferential face thereof and an attaching portion provided in the inside thereof on the distal end side with respect to the opening, the inner tube being disposed such that the inner tube can move in an axial direction with respect to the outer tube between a proximal end side position of the opening and the attaching portion, the inner tube having a cutting unit provided in the hollow inside of the distal end side end portion thereof and the inner tube being capable of attaching to the attaching portion of the outer tube.

With the catheter system of the disclosure herein, a thrombus suctioned out to the opening can be cut off by the inner tube and is further pressed against the attaching portion and is then cut into thrombus pieces having a size smaller than the inner diameter of the inner tube by the cutting unit. Therefore, it is possible to crush the thrombus into thrombus pieces smaller than the inner diameter of the inner tube with certainty and thereby suppress the thrombus from clogging the inside of the shaft main body.

DETAILED DESCRIPTION

An exemplary embodiment of the disclosure herein is described with reference to the accompanying drawings. A catheter system 10 of the exemplary embodiment is inserted into a blood vessel in deep venous thrombosis and is used for treatment of removing a thrombus. Note that the size ratio of each figure is sometimes exaggerated and different from an actual size ratio for the convenience of illustration. Note that, in the present specification, the side of a shaft main body 11 for being inserted into a body lumen is referred to as "distal end" or "distal end side," and the side of the shaft main body 11 for being operated by a hand is referred to as "proximal end" or "proximal end side."

Figure 1:
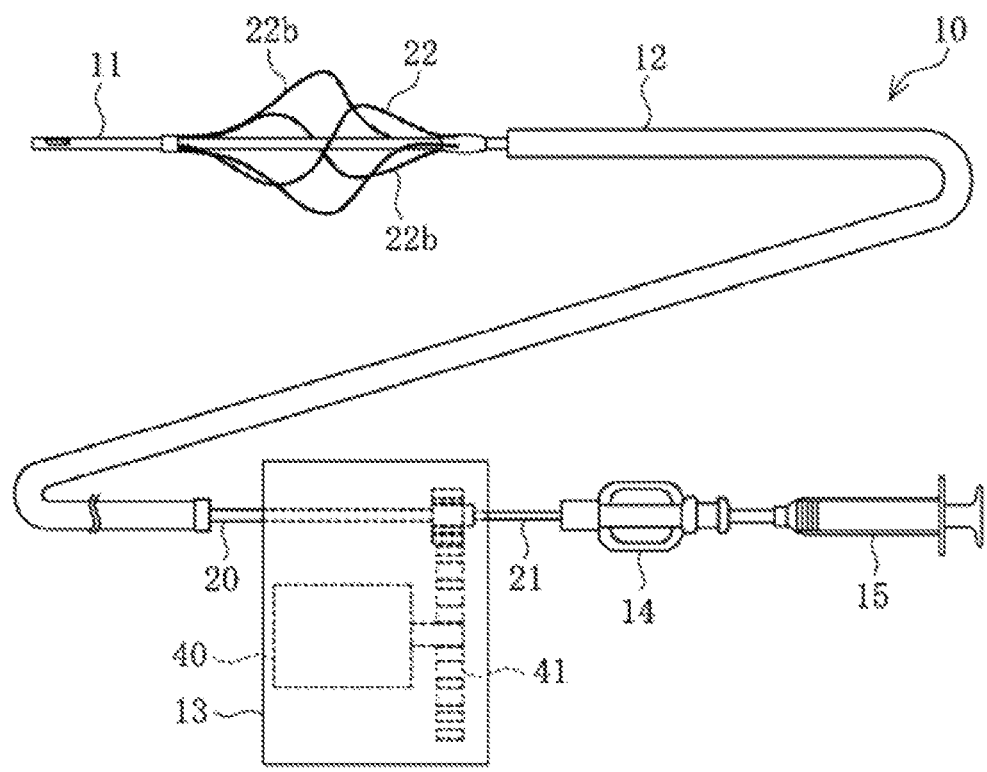
FIG. 1 is schematic front elevational view depicting a general structure of a catheter system according to an exemplary embodiment of the disclosure.

Referring first to FIG. 1, the catheter system 10 includes a shaft main body 11, an outermost sheath member 12, a rotational driving unit 13, a hub 14 and a syringe 15. The shaft main body 11 is formed in an elongated form, and the outermost sheath member 12 accommodates the shaft main body 11 therein and is slidably moveable in an axial direction thereof with respect to the shaft main body 11. The rotational driving unit 13 is capable of rotating the shaft main body 11. The hub 14 is provided at a proximal end side end portion of the shaft main body 11, and the syringe 15 is connected to the proximal end side of the hub 14.

The shaft main body 11 is configured from an outer tube 20 and an inner tube 21 each formed in an elongated hollow form. Each of the outer tube 20 and the inner tube 21 has a lumen in the inside thereof. The inner diameter of the outer tube 20 is greater than the outer diameter of the inner tube 21, and the inner tube 21 is accommodated in the hollow inside of the outer tube 20. Further, the inner tube 21 is movable in an axial direction with respect to the outer tube 20.

The outer tube 20 has a distal end side end portion formed as a distal end portion of the shaft main body 11 and a proximal end side end portion positioned on the rotational driving unit 13. The inner tube 21 extends, at a proximal end side end portion thereof, farther than the proximal end side end portion of the outer tube 20 and is connected to the hub 14. The hollow inside of the inner tube 21 can be suctioned into a negative pressure state by the syringe 15 connected to the hub 14.

The outer tube 20 and the inner tube 21 are formed from a material which is flexible and has a property that it can transmit power of rotation acting from the proximal end side thereof to the distal end side. For example, a tube in the form of a multi-layer coil such as a three-layer coil configured from coils having alternate winding directions like right-, left- and right-handed winding directions or an article formed from a material including, for example, polyolefin such as polyethylene or polypropylene, polyester such as polyamide or polyethylene terephthalate, fluorine-containing polymer such as ETFE, PEEK (polyether ether ketone), polyimide or a combination of them and a reinforcing member such as a wire embedded in the material is used.

Although the constituent material of the outermost sheath member 12 is not particularly limited, by way of example, polyolefin such as polyethylene or polypropylene, polyester such as polyamide or polyethylene terephthalate, fluorine-containing polymer such as ETFE, PEEK (polyether ether ketone) or polyimide can be suitably used. The outermost sheath member 12 may alternatively be configured from a plurality of materials or may have a reinforcing member such as a wire embedded therein.

Figure 2:
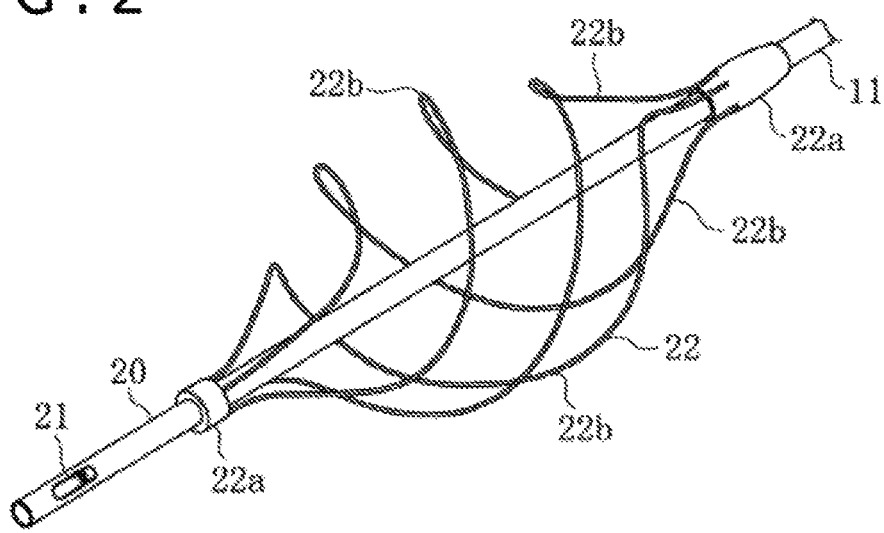
FIG. 2 is a perspective view of a portion of the catheter system shown in FIG. 1 in the proximity of a distal end portion of a shaft main body including a stirring portion.

A stirring unit 22 is provided at a distal end portion of the outer tube 20. The stirring unit 22 has two base portions 22a provided on the proximal end side and the distal end side and configured to be fixed to an outer circumferential surface of the outer tube 20. A plurality of spiral portions 22b extend between the base portions 22a. The spiral portions 22b are individually twisted in the same direction along the axial direction and are disposed such that fixed positions thereof to the base portions 22a are different in a circumferential direction from each other and positions thereof in the axial direction thereof at which they are curved are different from each other. Consequently, the stirring unit 22 is formed so as to have a shape such that it has uniform swelling in a circumferential direction as a whole as depicted in FIG. 2. If the outer tube 20 rotates, then also the stirring unit 22 is rotated by the rotation of the outer tube 20, whereby the stirring unit 22 can crush a thrombus or stir crushed thrombus pieces.

Each spiral portion 22b which configures the stirring unit 22 is formed from a thin wire of metal having flexibility. Before the shaft main body 11 is inserted into a target region, the stirring unit 22 remains in a state in which it is accommodated in the inside of the outermost sheath member 12. After the shaft main body 11 is inserted into the target region, if the outermost sheath member 12 is slidably moved to the proximal end side, then the stirring unit 22 is exposed outside of the outermost sheath member 12 and expanded to such a shape as depicted in FIG. 1. Therefore, the spiral portions 22b are preferably formed from a material having a shape memory property. For the spiral portions 22b, a shape memory alloy, stainless steel or the like to which a shape memory effect or hyperelasticity can be provided by heat treatment can be suitably used. As the shape memory alloy, Ni—Ti-based, Cu—Al—Ni-based and Cu—Zn—Al-based alloys and combinations of them are preferably used.

The rotational driving unit 13 includes a drive motor 40 and a gear unit 41 for interlocking the drive motor 40 with the outer tube 20 of the shaft main body 11. The rotational driving unit 13 can rotate the outer tube 20 in a circumferential direction by energizing the drive motor 40 to rotate. In the exemplary embodiment, the outer tube 20 is driven by the drive motor 40 such that it rotates alternately in two directions, a positive and a negative direction of a circumferential direction (i.e., clockwise and counter-clockwise). As the outer tube 20 is rotated alternately toward the two positive and negative directions, the blood flow can be directed alternately to the opposite directions.

Figure 3:
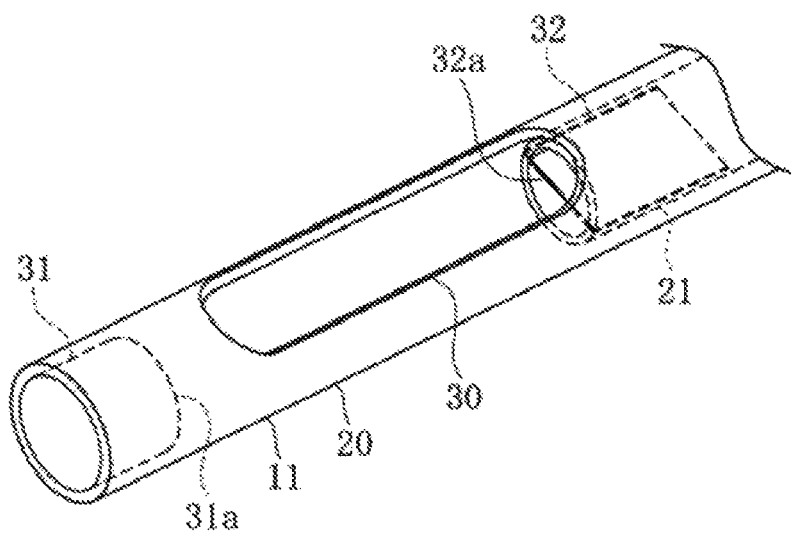
FIG. 3 is an enlarged perspective view of portions of the catheter system shown in FIG. 1 in the proximity of distal end portions of an outer tube and an inner tube.

The structure of a distal end portion of the shaft main body 11, as depicted in FIG. 3, includes an opening 30 in the form of an elongated hole is formed in an axial direction at a portion of the outer tube 20 in the proximity of the distal end portion such that the outside and the inside of the outer tube 20 are communicated with each other therethrough. A cylindrical attaching portion 31 is provided at a distal end portion of the outer tube 20 so that the distal end of the outer tube 20 is closed up by the attaching portion 31. A proximal end side face of the attaching portion 31 serves as an attaching face 31a which is opposed to a distal end side face of the inner tube 21. The attaching face 31a is positioned on the distal end side with respect to the distal end side end portion of the opening 30 of the outer tube 20. The attaching portion 31 is formed from stainless steel or the like.

The inner tube 21 has a distal end side end face positioned at the position of the distal end side end portion of the opening 30 of the outer tube 20 or at a position on the proximal end side with respect to the position of the distal end side end portion of the opening 30. A cutting unit 32 is formed from a thin plate made of a metal and has a width corresponding to the diameter of the inner tube 21. The cutting unit 32 has an incisive blade portion 32a formed at the distal end thereof.

Figure 4:
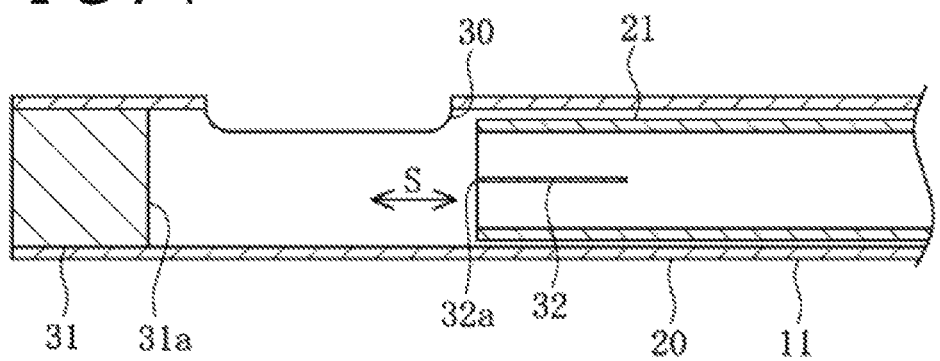
FIG. 4 is a sectional view of the catheter system shown in FIG. 1 taken along a center axis depicting portions in the proximity of distal end portions of the outer tube and the inner tube.

As depicted in FIG. 4, the blade portion 32a and the inner tube 21 are disposed such that distal end side end faces thereof have no step therebetween. Therefore, if the distal end face of the inner tube 21 attaches to the attaching face 31a of the attaching portion 31, then the blade portion 32a also attaches to the attaching face 31a. The inner tube 21 is slidably movable with respect to the outer tube 20 in a direction indicated by an arrow mark S, namely, along an axial direction, at least from the position depicted in FIG. 4 to another position at which the inner tube 21 attaches to the attaching face 31a of the attaching portion 31. A distal end portion of the inner tube 21 may have a thickness smaller than the thickness of the inner tube 21 other than the distal end portion (that is, a thickness which is the difference of the inner pipe inner diameter from the inner pipe outer diameter) and similar to the thickness of the blade portion 32a of the cutting unit 32.

Figure 5:
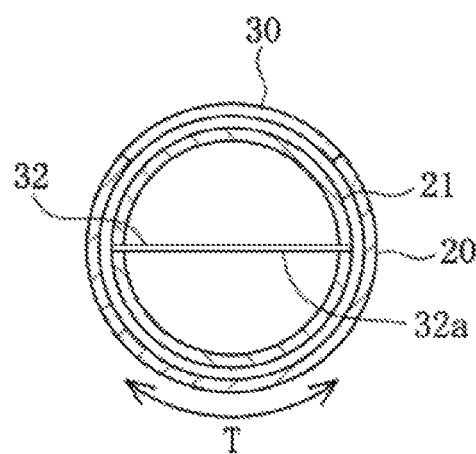
FIG. 5 is a cross sectional view of the catheter system shown in FIG. 1 taken along a plane orthogonal to the center axis at a position of an opening depicting the outer tube and the inner tube.

As depicted in FIG. 5, the outer tube 20 and the inner tube 21 are disposed coaxially with each other, and the outer tube 20 can be moved back and forth in the direction indicated by an arrow mark T, namely, in a circumferential direction, by the rotational driving unit 13. However, the outer tube 20 is not limited to that which moves back and forth but may be an outer tube which rotates in one direction. The cutting unit 32 is disposed such that it equally divides the sectional shape of the hollow portion of the inner tube 21 into two portions.

A method of use of the catheter system 10 of the exemplary embodiment is described below taking a case in which it is used to suction a thrombus in a blood vessel. At a stage before the shaft main body 11 is inserted into a blood vessel, a distal end portion of the shaft main body 11 including the stirring unit 22 is in a state in which it is accommodated in the outermost sheath member 12 as described hereinabove.

Before the shaft main body 11 of the catheter system 10 of the exemplary embodiment is inserted, a protective member such as a balloon for limiting communication of liquid in the blood vessel is preferably disposed in one or both of the extremity side and the insertion side with respect to the thrombus in the blood vessel. This can prevent crushed thrombus pieces from flowing in the blood vessel and moving to a different place.

Figure 6:
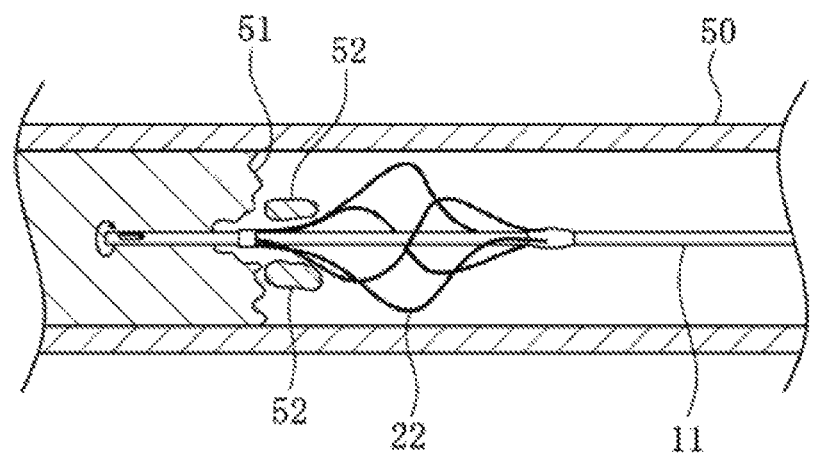
FIG. 6 is a sectional view of a portion of the catheter system shown in FIG. 1 in the proximity of a distal end portion of the shaft main body illustrating a state in which the distal end portion of the shaft main body is inserted to a position of a thrombus in a blood vessel and the shaft main body is rotated in one direction.

First, as depicted in FIG. 6, the distal end portion of the shaft main body 11 is moved to the position of a thrombus 51 of a blood vessel 50. If, in the state in which the stirring unit 22 is inserted to the position of the thrombus 51, the outer tube 20 is rotated in the direction indicated by an arrow mark in FIG. 6 by the rotational driving unit 13, then the stirring unit 22 is also rotated by the rotation of the outer tube 20. Consequently, the thrombus which is in a fixed state in the blood vessel 50 is crushed into thrombus pieces 52.

Figure 7:
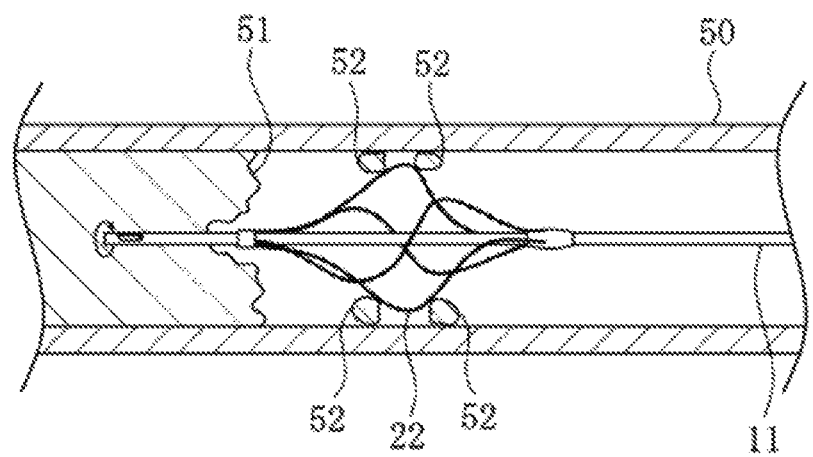
FIG. 7 is a sectional view of a portion of the catheter system shown in FIG. 1 in the proximity of a distal end portion of the shaft main body illustrating a state in which thrombus pieces sandwiched between a stirring portion and a blood vessel wall are cut by rotation of the outer tube.
Figure 8:
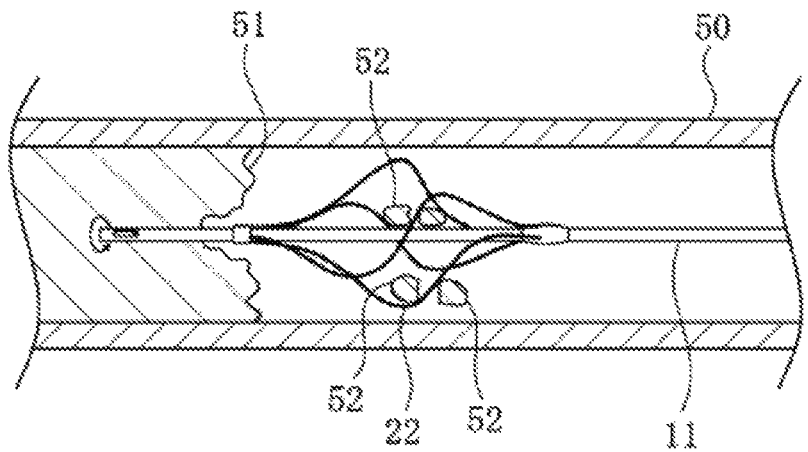
FIG. 8 is a sectional view of a portion of the catheter system shown in FIG. 1 in the proximity of a distal end portion of the shaft main body illustrating a state in which thrombus pieces are cut by the stirring portion whose relative speed with respect to the thrombus is increased by reverse rotation of the outer tube.

The thrombus pieces 52 crushed by the stirring unit 22 move to the blood vessel wall side by centrifugal force generated in the blood flow by the rotating stirring unit 22. As depicted in FIG. 7, the thrombus pieces 52 are sandwiched between an outermost peripheral portion of the stirring unit 22 and the blood vessel wall and are cut there by the stirring unit 22. Further, when the outer tube 20 is rotated in the opposite direction to that depicted in FIG. 6 as depicted in FIG. 8, the relative speed of the stirring unit 22 to the crushed thrombus pieces 52 increases. Thus, the thrombus pieces 52 can be further cut.

Figure 9:
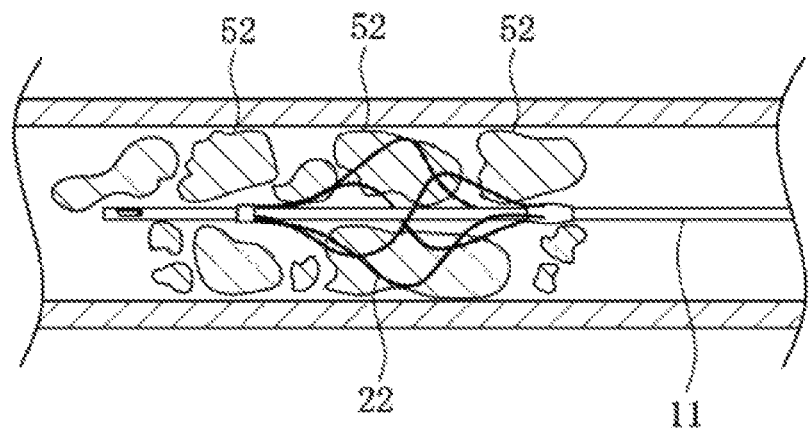
FIG. 9 is a sectional view of a portion of the catheter system shown in FIG. 1 in the proximity of a distal end portion of the shaft main body illustrating a state in which the thrombus fixed to a blood vessel is crushed by the stirring portion.

If the rotation of the stirring unit 22 is continued, then the entire thrombus 51 fixed in the blood vessel 50 can be cut into thrombus pieces 52 which are crushed as depicted in FIG. 9, and the crushed thrombus pieces 52 are swirled up without precipitating or the like in the blood vessel 50. Further, since the stirring unit 22 has the spiral portions 22b which have a directionality toward the distal end side, the thrombus pieces 52 caught by the stirring unit 22 move toward the distal end side of the shaft main body 11 as the stirring unit 22 rotationally moves back and forth.

Figure 10:
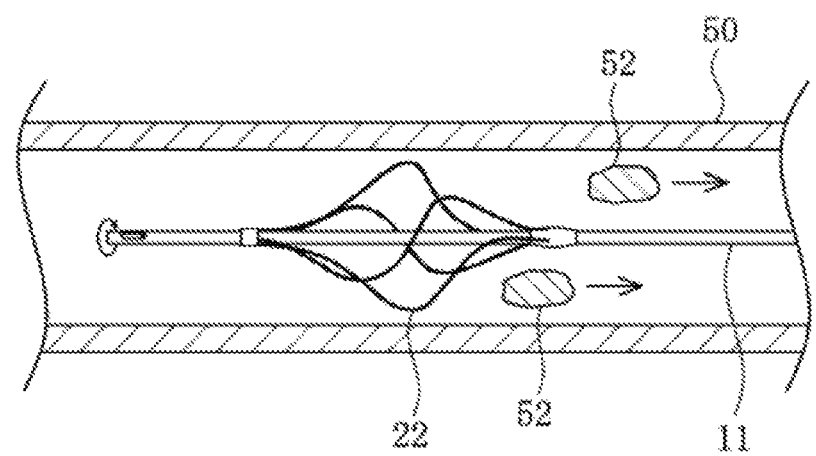
FIG. 10 is a sectional view of a portion of the catheter system shown in FIG. 1 in the proximity of a distal end portion of the shaft main body illustrating a state in which crushed thrombus pieces move towards the proximal end side by the stirring portion.
Figure 11:
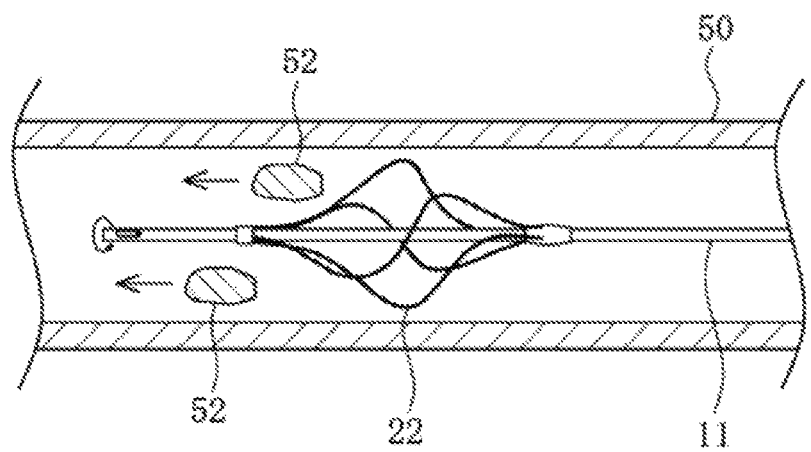
FIG. 11 is a sectional view of a portion of the catheter system shown in FIG. 1 in the proximity of a distal end portion of the shaft main body illustrating a state in which crushed thrombus pieces move towards the distal end side by the stirring portion.

Some of the crushed thrombus pieces 52 sometimes move toward the proximal end side from the stirring unit 22 as depicted in FIG. 10, and if this occurs, then the thrombus pieces 52 cannot be suctioned from the distal end portion of the shaft main body 11. However, the outer tube 20 rotates alternately toward the two positive and negative directions as described hereinabove. Consequently, since the blood flow is directed alternately toward the opposite directions, the thrombus pieces 52 moving toward the proximal end side from the stirring unit 22 are also moved to the distal end side with the blood flow as depicted in FIG. 11. The thrombus pieces 52 can thus be suctioned from the distal end portion of the shaft main body 11.

Figure 12:
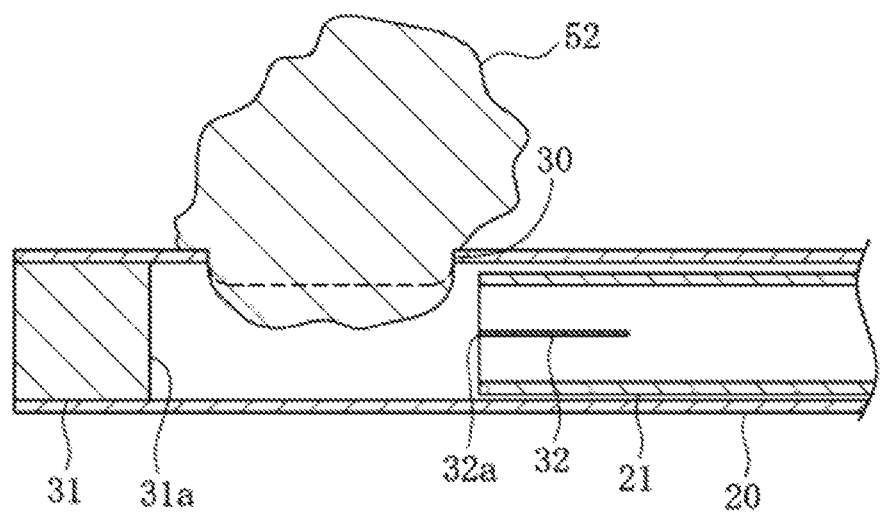
FIG. 12 is an enlarged sectional view of portions of the catheter system shown in FIG. 1 in the proximity of distal end portions of the outer tube and the inner tube illustrating a state in which crushed thrombus pieces are sucked to an opening of the outer tube.

In order to remove the thrombus pieces, the plunger in the syringe 15 is moved proximally to place the hollow inside of the inner tube 21 into a negative pressure state. The distal end side end portion of the inner tube 21 is communicated with the hollow inside of the outer tube 20, and the outer tube 20 is further communicated with the outside of the shaft main body 11 through the opening 30. Therefore, the opening 30 generates a suction force to the outside of the shaft main body 11 and draws the crushed thrombus pieces 52 floating in the blood vessel 50. As depicted in FIG. 12, the thrombus pieces 52 drawn to the opening 30 form a mass and partly enter the hollow inside of the outer tube 20.

Figure 13:
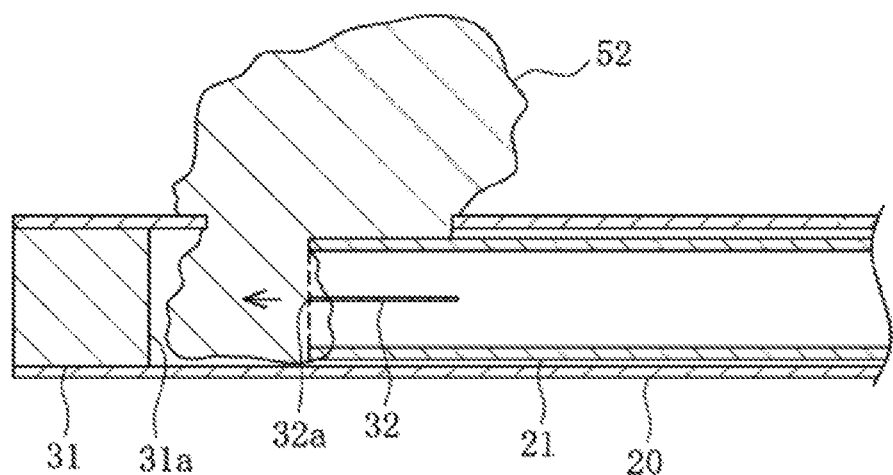
FIG. 13 is an enlarged sectional view of portions of the catheter system shown in FIG. 1 in the proximity of distal end portions of the outer tube and the inner tube illustrating a process in which the thrombus mass sucked to the opening of the outer tube is cut off by the inner tube.

After the syringe 15 is drawn, the inner tube 21 is moved in an axial direction with respect to the outer tube 20. In FIG. 12, since the inner tube 21 has been positioned on the proximal end side with respect to the opening 30, the inner tube 21 is moved toward the distal end side of the outer tube 20, namely, in a direction toward the attaching portion 31. Consequently, the thrombus mass 52 entering the hollow inside of the outer tube 20 through the opening 30 is partly compressed and cut off by the distal end face of the inner tube 21 as depicted in FIG. 13.

Figure 14:
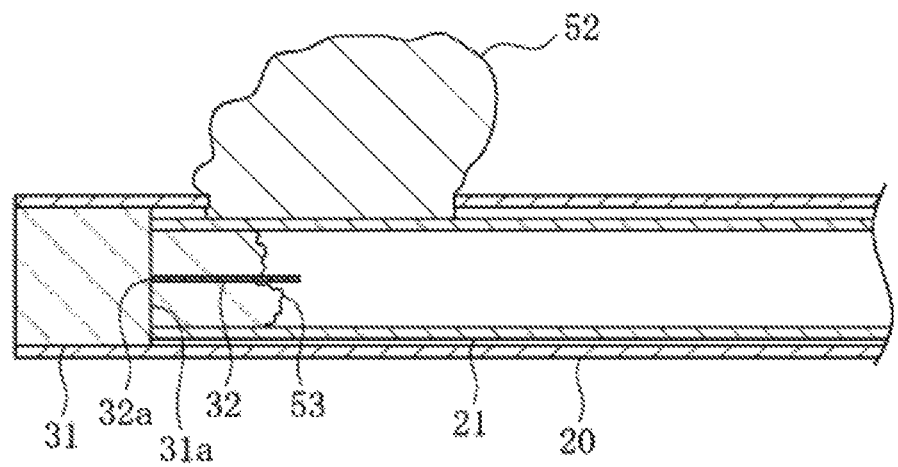
FIG. 14 is an enlarged sectional view of portions of the catheter system shown in FIG. 1 in the proximity of distal end portions of the outer tube and the inner tube illustrating a state in which the thrombus mass cut off by the inner tube is cut by a cutting unit.

If the inner tube 21 is further moved until the distal end face of the inner tube 21 attaches to the attaching face 31a of the attaching portion 31, then the cut-off thrombus mass 53 is accommodated into the hollow inside of the inner tube 21 as depicted in FIG. 14. Thereupon, the thrombus mass 53 is cut into two pieces by the blade portion 32a of the cutting unit 32 provided at the distal end portion of the inner tube 21. As the inner tube 21 attaches to the attaching face 31a of the attaching portion 31, the blade portion 32a also attaches to the attaching face 31a, and thus the thrombus mass 53 cut off in the hollow inside of the outer tube 20 is pressed against the attaching portion 31 and cut by the blade portion 32a. Therefore, the cut-off thrombus mass 53 can be cut with certainty into pieces of a size smaller than the inner diameter of the inner tube 21. Consequently, the cut thrombus pieces 54 can be prevented from clogging in the hollow inside of the inner tube 21 (see FIG. 15).

Figure 15:
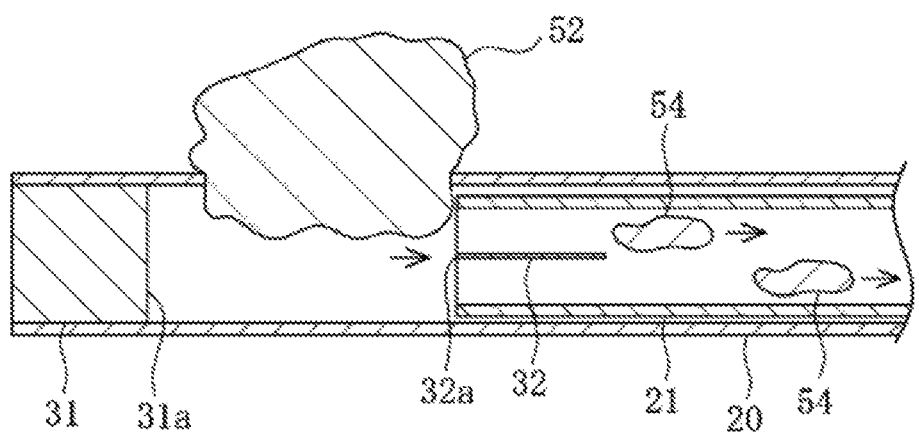
FIG. 15 is an enlarged sectional view of portions of the catheter system shown in FIG. 1 in the proximity of distal end portions of the outer tube and the inner tube illustrating a process in which the thrombus mass cut by the cutting unit is sucked to the proximal end side of the inner tube.

Since the hollow inside of the inner tube 21 is kept in the negative pressure state by the syringe 15, the cut thrombus pieces 54 move toward the proximal end side in the hollow inside of the inner tube 21 as depicted in FIG. 15. Further, the inner tube 21 is moved toward the proximal end side away from the attaching portion 31, so that the opening 30 is opened again and the thrombus mass 52 is suctioned to enter the hollow inside of the outer tube 20. Accordingly, by repeating the reciprocating movement of the inner tube 21 in the axial direction, the thrombus mass 52 can be cut finely and successively suctioned out.

While the crushed thrombus mass 52 is suctioned by the shaft main body 11, preferably the rotational movement of the outer tube 20 is continued. Since the outer tube 20 is rotating, swirling current is generated in the blood flow in the blood vessel 50 and is likely to concentrate in the proximity of the center of rotation, namely, in the proximity of the center of the blood vessel in a diametrical direction, the thrombus mass 52 is likely to be suctioned from the opening 30. Further, swirling current generated in the proximity of the opening 30 influences the flow in the hollow inside of the inner tube 21 and swirling flow is also generated in the inside of the inner tube 21. By this, the flow resistance in the axial direction is reduced in the inside of the inner tube 21, and the cut thrombus pieces 54 can be smoothly suctioned.

In the exemplary embodiment, during suction of the thrombus mass 52, the outer tube 20 rotationally moves and the inner tube 21 moves back and forth in the axial direction with respect to the outer tube 20. However, the outer tube 20 and the inner tube 21 may perform an additional movement. For example, if the inner tube 21 performs an additional movement of rotationally moving in a different manner relative to the outer tube 20 (the direction of the rotation is the opposite direction or, although the direction of the rotation is same, the speed of the rotation is different), then the thrombus pieces 52 suctioned into the opening 30 can be cut with certainty and introduced into the hollow inside of the outer tube 20. Further, by adding back and forth movement of the outer tube 20, the thrombus 51 in a greater range can be stirred, that is, a greater portion of the thrombus can be stirred.

As a combination of movements of the outer tube 20 and the inner tube 21 including such additional movements, the following combinations are available. Note that, in any case, the movements include a movement of the inner tube 21 which moves back and forth in the axial direction with respect to the outer tube 20. For example, (1) a combination movement wherein the outer tube 20 rotationally moves and the inner tube 21 moves back and forth in the axial direction with respect to the outer tube 20 and rotationally moves in a different manner relative to the outer tube 20; (2) another combination movement wherein the outer tube 20 moves back and forth in the axial direction and the inner tube 21 moves back and forth in the axial direction with respect to the outer tube 20; (3) a further combination movement wherein the outer tube 20 moves back and forth in the axial direction and the inner tube 21 moves back and forth in the axial direction with respect to the outer tube 20 and rotationally moves with respect to the outer tube 20; (4) a still further combination movement wherein the outer tube 20 moves rotationally and moves back and forth in the axial direction and the inner tube 21 moves back and forth in the axial direction with respect to the outer tube 20; (5) a further combination movement wherein the outer tube 20 moves rotationally and moves back and forth in the axial direction and the inner tube 21 moves back and forth in the axial direction with respect to the outer tube 20 and rotationally moves in a different manner relative to the outer tube 20; and so forth are available.

By the above-described combination movements including the combination movement of the outer tube 20 and the inner tube 21 of the exemplary embodiment, the thrombus 51 is crushed and stirred in the blood vessel 50 and suctioned from the opening 30, whereafter it is cut by the cutting unit 32 and sent to the proximal end side of the shaft main body 11 and then removed from within the blood vessel 50.

In the exemplary embodiment, the speed of rotation of the outer tube 20 is equal to or higher than 1000 rpm and the speed of movement of the shaft main body 11 in the proximity of a thrombus is equal to or lower than 1 mm/second. However, the catheter system may be used in conditions other than the conditions described for the exemplary embodiment.

After the thrombus 51 is removed, the back and forth movement and the rotational movement of the outer tube 20 and the inner tube 21 are stopped. Then, the outermost sheath member 12 is moved in the axial direction so as to accommodate the stirring unit 22, and the shaft main body 11 is pulled out from the blood vessel 50, thereby completing the treatment.

While, in the exemplary embodiment, the thrombus 51 in the blood vessel 50 is crushed by the stirring unit 22 of the shaft main body 11, a drug for dissolving the thrombus 51 may additionally be used. Further, the shaft main body 11 may not have the stirring unit 22. In this case, the thrombus 51 is crushed in advance by some other means, and if the shaft main body 11 is inserted and the outer tube 20 and the inner tube 21 are driven, then the crushed thrombus mass 52 can be suctioned. Also where the shaft main body 11 does not have the stirring unit 22, if the outer tube 20 is rotated, then swirling flow can be generated in the blood vessel 50 to achieve the effect described hereinabove. Further, where the shaft main body 11 does not have the stirring unit 22, by driving the outer tube 20 to rotate alternately in the two positive and negative directions in a circumferential direction, the crushed thrombus pieces 52 can be prevented from sticking to the outer tube 20.

Figure 16:
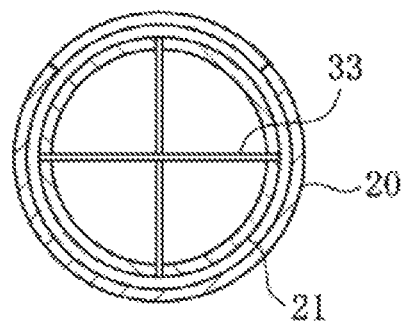
FIG. 16 is a sectional view of the outer tube and the inner tube of the catheter system shown in FIG. 1 at a position of the opening depicting a modification to the cutting unit.

A modification to the cutting portion is now described. The cutting unit 32 described above is formed from a single thin plate and disposed so as to divide the hollow section of the inner tube 21 into two parts. However, a cutting unit 33 formed from two thin plates being configured to be substantially orthogonal to each other may be alternatively disposed as depicted in FIG. 16 so that the hollow section of the inner tube 21 is divided into four parts. The number of thin plates for the cutting portion may be further increased, as would be appreciated by one skilled in the art.

Further, though not depicted, the cutting portion may have a shape having a recessed or projected portion at a distal end portion thereof. In this case, the recessed or projected portion corresponding to the cutting portion is preferably provided on an attaching portion to which the cutting portion is to attach so that a gap may not be generated between the cutting portion and the attaching portion. This makes it possible to crush the cut-off thrombus mass 53 with certainty and cut the thrombus mass 53 by the cutting portion. Further, although the distal end side end face of the cutting unit 32 in the exemplary embodiment is disposed so as to be flush with the distal end side end face of the inner tube 21 without an offset therebetween, it may otherwise project from the distal end side end face of the inner tube 21 to the distal end side.

Figure 17:
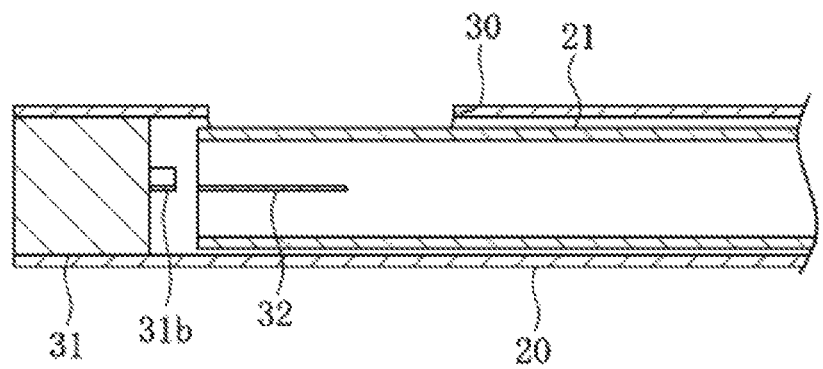
FIG. 17 is an enlarged sectional view of a portion of the catheter system shown in FIG. 1 in the proximity of a distal end portion of the outer tube and the inner tube depicting a modification to an attaching portion.

A modification to the attaching portion is now described with reference to FIG. 17. While the attaching portion 31 described hereinabove has the attaching face 31a in the form of a flat face on the proximal end side thereof, a further blade portion 31b may also be provided on the attaching portion such that the blade portion 31b of the attaching portion 31 and the blade portion 32a of the inner tube 21 may attach to each other. By the configuration just described, the blade portions abut with each other, the thrombus mass 53 can be cut more readily. Further, as another modification, the attaching portion may be formed from two layers. In this case, from between the two layers which form the attaching portion, the layer on the proximal portion side is configured from a stainless steel plate and the layer on the distal end side is configured from silicone rubber. In this case, the silicone rubber plays a role of a damper, and the blade portion attaches in a plane to the attaching portion with certainty. Consequently, a thrombus can be cut with certainty.

As described above, according to the disclosure herein, the catheter system 10 includes a shaft main body 11 including an elongated hollow outer tube 20 and an inner tube 21 accommodated in the inside of the elongated hollow outer tube 20, the hollow inside of the inner tube 21 being suctioned from the proximal end side thereof by a syringe or other means for creating a negative pressure, the outer tube 20 having an opening 30 formed in a circumferential face thereof and an attaching portion 31 provided in the inside thereof on the distal end side with respect to the opening 30, the inner tube 21 being disposed such that the inner tube 21 can move in an axial direction with respect to the outer tube 20 and at least a distal end side end portion thereof can move back and forth between a proximal end side position with respect to the opening 30 and the attaching portion 31, the inner tube 21 having a cutting unit 32 provided in the hollow inside of the distal end side end portion thereof and capable of attaching to the attaching portion 31 of the outer tube 20. Therefore, a thrombus mass 52 suctioned to the opening 30 can be cut off by the inner tube 21 and then the resulting thrombus mass 53 is pressed against the attaching portion 31 to be cut into thrombus pieces 54 having a size smaller than the inner diameter of the inner tube 21 by the cutting unit 32. Therefore, it is possible to crush the suctioned thrombus mass 52 into thrombus pieces 54 smaller than the inner diameter of the inner tube 21 with certainty and thereby prevent the thrombus pieces 54 from clogging the inside of the shaft main body 11.

If the catheter system 10 is configured such that the outer tube 20 is driven to rotate in a circumferential direction, then it is possible to generate swirling current in the body lumen by the outer tube 20 to stir the thrombus pieces 52, to thereby allow the thrombus pieces 52 to be suctioned readily to the opening.

If the catheter system 10 is configured such that the outer tube 20 is driven to rotate alternately toward two positive and negative directions in the circumferential direction, then such a situation that the thrombus pieces 52 stick to the outer tube 20 and become less likely to be suctioned from the opening 30 can be prevented.

If the catheter system 10 is configured such that the outer tube 20 has a stirring unit 22 for stirring the inside of a body lumen, then the stirring effect in the body lumen by rotation of the outer tube 20 can be increased and the thrombus can be crushed.

If the catheter system 10 is configured such that the stirring unit 22 includes a spiral portion 22b along an axial direction of the outer tube 20, then the thrombus pieces 52 can be guided to the opening 30 side by the rotation of the stirring unit 22.

Further, if the catheter system 10 is configured such that the cutting unit 32 has a blade portion 32a at a distal end portion thereof, and the blade portion 32a attaches to the attaching portion 31 of the outer tube 20, then the thrombus mass 53 can be cut into small thrombus pieces with certainty.

Further, if the catheter system 10 is configured such that the blade portion of the cutting unit has a distal end face which lies flush with the distal end face of the inner tube, and the attaching portion has an attaching face to which both the blade portion and the distal end face of the inner tube attach, then the thrombus mass 53 entering the outer tube 20 can be pressed against the attaching face 31a and cut by the blade portion 32a. Consequently, cutting of the thrombus mass 53 can be performed with a higher degree of certainty.

The disclosure herein further provides a treatment method for suctioning and removing an object generated in a lesion region in a body lumen. The treatment method is performed using a catheter system 10 which includes a shaft main body 11 including an elongated hollow outer tube 20 and an inner tube 21 accommodated in the inside of the elongated hollow outer tube 20. The hollow inside of the inner tube 21 is suctioned from the proximal end side thereof. The outer tube 20 has an opening 30 formed in a circumferential face thereof and an attaching portion 31 provided in the inside thereof on the distal end side with respect to the opening 30. The inner tube 21 is disposed such that the inner tube 21 can move in an axial direction with respect to the outer tube 20 and at least a distal end side end portion thereof can move back and forth between a proximal end side position with respect to the opening 30 and the attaching portion 31. The inner tube 21 has a cutting unit 32 provided in the hollow inside of the distal end side end portion thereof, the cutting unit 32 being capable of attaching to the attaching portion 31 of the outer tube 20. The treatment method includes the steps of (i) inserting the shaft main body 11 into a body lumen until a distal end portion thereof attaches to the lesion region, (ii) suctioning the hollow inside of the inner tube 21 to place the hollow inside into a negative pressure state, (iii) moving a distal end side end portion of the inner tube 21 to the attaching portion 31 so as to cut a thrombus suctioned to the opening 30 and cutting the thrombus by the cutting unit 32 such that the cut thrombus pieces have a size smaller than an inner diameter of the inner tube 21, (iv) returning the distal end side end portion of the inner tube 21 to the proximal end side position of the opening 30, (v) repeating the steps of (iii) and (iv), and (vi) removing the shaft main body 11 from the inside of the body lumen. With the treatment method, it is possible to suction (draw) a thrombus mass to the opening 30, cut off the thrombus mass by the inner tube 21, further press the thrombus mass against the attaching portion 31 and then cut thrombus mass into thrombus pieces having a size smaller than the inner diameter of the inner tube 21 by the cutting unit 32. Therefore, it is possible to crush the suctioned thrombus mass into thrombus pieces smaller than the inner diameter of the inner tube 21 with certainty and thereby prevent the thrombus from clogging the inside of the shaft main body 11.

In the treatment method described above, after the step of inserting the shaft main body 11 into the body lumen until the distal end portion thereof attaches to the lesion region, the outer tube 20 may be rotated in a circumferential direction or moved in the axial direction. By this, it is possible to suction the thrombus to the opening 30 and remove the thrombus over a wide range in the blood vessel. Further, before or after the step (iv), a step may be provided for rotating the inner tube 21 to rotate the cutting unit 32 to move the position on the attaching face 31a at which the cutting unit 32 and the attaching unit 31 make contact with each other in a radial direction. By the step just described, the cutting unit 32 is prevented from continuously contacting the same position on the attaching face 31a, and the thrombus can be cut more finely.

Further, in the treatment method described above, when the outer tube 20 is rotated in a circumferential direction, the outer tube 20 may be rotated alternately in the two positive and negative directions in the circumferential direction. This makes it possible to suppress such a situation that a thrombus sticks to the outer tube 20 and cannot be sent to the opening 30 side.

Further, in the treatment method described above, a stirring unit 22 for stirring the inside of the body lumen may be provided with the outer tube 20 such that, by rotating the stirring unit 22 together with the outer tube 20, an object in the inside of the body lumen is crushed and stirred in the body lumen. This makes it possible to perform the crushing and the suction of a thrombus by a single medical device, and consequently, the time and labor necessary for the treatment can be reduced.

Note that the disclosure herein is not limited only to the exemplary embodiments described hereinabove but can be modified or altered in various manners by those skilled in the art without departing from the spirit and scope of the present disclosure. For example, in the exemplary embodiment, the outer tube 20 is driven to rotate by the rotational driving unit 13 having the driving motor 40. However, the driving source is not particularly limited and may be, for example, a gas turbine which is rotated by high-pressure gas such as high-pressure nitrogen gas. Further, while the inner tube 21 is movable in the axial direction with respect to the outer tube 20 and is manually moved back and forth in the axial direction, the inner tube 21 may otherwise be driven by a driving source such as a motor through a crank member or the like.

Further, while, in the exemplary embodiment, the stirring unit 22 is provided on the outer tube 20, the shape of the stirring unit 22 is not limited to that of the exemplary embodiment. Also it is possible to form the catheter system 10 without including the stirring unit 22. Where the stirring unit 22 is not provided, by rotating the outer tube 20 alternately in the two positive and negative directions in the circumferential direction, the thrombus pieces 52 can be prevented from sticking to the outer tube 20. Consequently, the thrombus pieces 52 can be prevented from remaining in the body lumen.

Further, while, in the exemplary embodiment, the opening 30 is formed at a position on the distal end side with respect to the stirring unit 22 in the axial direction of the outer tube 20, the position of the opening 30 is not limited thereto. The opening 30 may be formed at the position of the stirring unit 22 in the axial direction of the outer tube 20 or at a position on the proximal end side with respect to the stirring unit 22 in the axial direction of the outer tube 20. The attaching portion 31 may be disposed at another position in the proximity of the distal end side with respect to the distal end side end portion of the opening 30.

Further, while, in the exemplary embodiment, the inner tube 21 is accommodated as a medical tool in the inside of the outer tube 20, the element which is to be accommodated in the inside of the outer tube 20 may not necessarily be a tubular medical tool. For example, the medical tool may have such an elongated shape and have a cutting unit in the form of a spatula at a distal end portion thereof.

The detailed description above describes a catheter system and treatment method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter system, comprising:
a shaft main body including an elongated hollow outer tube and an inner tube accommodated inside of the elongated hollow outer tube, a hollow inside of the inner tube having an open distal end and configured to be suctioned from a proximal end side of the inner tube, the proximal end side of the inner tube configured to extend beyond a proximal end side of the outer tube and configured to be connected to a hub;
the outer tube having an opening formed in a circumferential surface of the outer tube and an attaching portion provided in the inside of the outer tube on a distal end side with respect to the opening, the attaching portion having a distal end and a proximal end, the proximal end of the attaching portion having an attaching surface having a flat surface extending orthogonal to a central axis of the outer tube and a blade portion projecting proximally from the attaching surface;
the inner tube being disposed such that the inner tube is configured to move in an axial direction with respect to the outer tube and at least a distal end side end portion of the inner tube is configured to move back and forth between a proximal end side position with respect to the opening and the attaching portion, the inner tube having a cutting unit arranged in the open distal end of the inner tube, a distal end portion of the cutting unit being provided within an interior of the hollow inside of the distal end side end portion of the inner tube and configured to contact the attaching portion of the outer tube, the cutting unit having a blade portion at the distal end portion of the cutting unit, the blade portion being formed from a plate having a first end and a second end, the first end of the plate and the second end of the plate being disposed on an inner surface of the inner tube and disposed so as to divide the hollow inside of the inner tube into parts, and wherein the blade portion of the inner tube is configured to abut the blade portion of the attaching portion of the outer tube; and the outer tube including a stirring unit for stirring the inside of a body lumen arranged proximal to the opening formed in a circumferential surface of the outer tube.

2. The catheter system according to claim 1, wherein the outer tube is driven to rotate in a circumferential direction.

3. The catheter system according to claim 2, wherein the outer tube is driven to rotate alternately toward two positive and negative directions in the circumferential direction.

4. The catheter system according to claim 1, wherein the stirring unit includes a plurality of spiral portions along an axial direction of the outer tube.

5. The catheter system according to claim 1, wherein the cutting unit has a width corresponding to a diameter of the inner tube.

6. The catheter system according to claim 1, wherein the blade portion of the cutting unit is formed from two thin plates disposed substantially orthogonal to each other so as to divide the hollow inside of the inner tube into four parts.

7. A treatment method wherein the catheter system according to claim 1 is used to suction and remove an object generated in a lesion region in a body lumen, comprising:
inserting the shaft main body into a body lumen until a distal end portion of the shaft main body attaches to the lesion region;
suctioning the hollow inside of the inner tube to place the hollow inside into a negative pressure state;
moving the distal end side end portion of the inner tube to the attaching portion so as to cut a thrombus suctioned to the opening and cutting the thrombus by the cutting unit such that the cut thrombus pieces have a size smaller than an inner diameter of the inner tube; and
removing the shaft main body from the inside of the body lumen.

8. The treatment method according to claim 7, further comprising, prior to the removing of the shaft main body from the inside of the body lumen:
returning the distal end side end portion of the inner tube to the proximal end side position of the opening; and
repeating the moving of the distal end side end portion of the inner tube to the attaching portion so as to cut a thrombus suctioned to the opening and cutting the thrombus by the cutting unit such that the cut thrombus pieces have a size smaller than an inner diameter of the inner tube, and the returning the distal end side end portion of the inner tube to the proximal end side position of the opening.

9. The treatment method according to claim 7, further comprising:
guiding the thrombus pieces to the opening by the rotation of the stirring unit.

10. The treatment method according to claim 7, wherein the outer tube moves rotationally and the inner tube moves back and forth in the axial direction with respect to the outer tube.

11. The treatment method according to claim 10, wherein the inner tube also moves rotationally in a different manner relative to the outer tube.

12. The catheter system according to claim 1, wherein the stirring unit has two base portions provided on a proximal end side and a distal end side, and wherein the two bases are configured to be fixed to an outer circumferential surface of the outer tube.

13. The catheter system according to claim 12, wherein the stirring unit includes a plurality of spiral portions arranged along an axial direction of the outer tube, each of the plurality of spiral portions being individually twisted in the same direction along the axial direction and are disposed such that fixed positions of the plurality of spiral portions to the two base portions are different in a circumferential direction from each other.

14. The catheter system according to claim 1, further comprising:
the hub provided at a proximal end side end portion of the shaft main body;
a syringe connected to a proximal end side of the hub; and
wherein the syringe is connected to a distal end hollow inside of the inner tube to be suctioned into a negative pressure state with the syringe.

15. The catheter system according to claim 1, wherein at least a portion of the attaching portion made from stainless steel.

16. A catheter system, comprising:
a shaft main body including an elongated hollow outer tube and an inner tube accommodated inside of the elongated hollow outer tube, a hollow inside of the inner tube having an open distal end and configured to be suctioned from a proximal end side of the inner tube, the proximal end side of the inner tube configured to extend beyond a proximal end side of the outer tube and configured to be connected to a hub;
wherein the outer tube has an opening formed in a circumferential surface of the outer tube and an attaching portion provided in an inside of the outer tube on a distal end side with respect to the opening, the attaching portion having a distal end and a proximal end, the proximal end of the attaching portion having an attaching surface having a flat surface extending orthogonal to a central axis of the outer tube and a blade portion projecting proximally from the attaching surface;
wherein the inner tube is disposed such that the inner tube is configured to move in an axial direction with respect to the outer tube and at least a distal end side portion of the inner tube is configured to move back and forth between a proximal end side position with respect to the opening and the attaching portion; and
wherein the inner tube includes a cutting unit arranged in the open distal end of the inner tube, a distal end portion of the cutting unit being provided within an interior of the hollow inside of the distal end side end portion of the inner tube and configured for attaching to the attaching portion of the outer tube, the cutting unit being configured to cut crushed thrombus pieces at the opening, the cutting unit having a blade portion at the distal end portion of the cutting unit, the blade portion disposed so as to divide the hollow inside of the inner tube into at least two parts, and wherein at least a portion of the blade portion of the inner tube is configured to abut the blade portion of the attaching portion of the outer tube.

17. The catheter system according to claim 16, wherein the outer tube is driven to rotate in a circumferential direction.

18. The catheter system according to claim 17, wherein the outer tube is driven to rotate alternately toward two positive and negative directions in the circumferential direction.

19. The catheter system according to claim 16, wherein the outer tube includes a stirring unit for stirring the inside of a body lumen arranged proximal to the opening formed in a circumferential surface of the outer tube, the stirring unit having two base portions provided on a proximal end side and a distal end side, and wherein the two bases are configured to be fixed to an outer circumferential surface of the outer tube; and wherein the stirring unit includes a plurality of spiral portions arranged along an axial direction of the outer tube, each of the plurality of spiral portions being individually twisted in the same direction along the axial direction and are disposed such that fixed positions of the plurality of spiral portions to the two base portions are different in a circumferential direction from each other.

* * * * *